(12) United States Patent
Hashikawa et al.

(10) Patent No.: US 10,426,732 B2
(45) Date of Patent: Oct. 1, 2019

(54) RAPIDLY DISINTEGRATING TABLET, AND METHOD FOR PRODUCING SAME

(71) Applicant: DAICEL CORPORATION, Osaka-shi, Osaka (JP)

(72) Inventors: Naohiro Hashikawa, Himeji (JP); Tomohito Okabayashi, Himeji (JP); Yoshihisa Takigawa, Himeji (JP); Atsuhiro Uetomo, Himeji (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 15/534,955

(22) PCT Filed: Oct. 28, 2015

(86) PCT No.: PCT/JP2015/080342
§ 371 (c)(1),
(2) Date: Jun. 29, 2017

(87) PCT Pub. No.: WO2016/103904
PCT Pub. Date: Jun. 30, 2016

(65) Prior Publication Data
US 2017/0333352 A1   Nov. 23, 2017

(30) Foreign Application Priority Data
Dec. 25, 2014 (JP) .................. 2014-261458

(51) Int. Cl.
*A61K 9/20* (2006.01)
*A61K 47/38* (2006.01)
*A61K 9/00* (2006.01)

(52) U.S. Cl.
CPC ............. *A61K 9/20* (2013.01); *A61K 9/0056* (2013.01); *A61K 9/2054* (2013.01); *A61K 9/2095* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 2004/0265375 | A1* | 12/2004 | Platteeuw | A61K 9/0056 424/464 |
| 2007/0078174 | A1* | 4/2007 | Flashner-Barak | A61K 31/433 514/363 |

FOREIGN PATENT DOCUMENTS

| | | |
|---|---|---|
| EP | 3 020 416 | 5/2016 |
| WO | 2004091585 | 10/2004 |

(Continued)

OTHER PUBLICATIONS

International Search Report of International Application No. PCT/JP/2015/080342 dated Jan. 19, 2016.

(Continued)

*Primary Examiner* — Robert A Wax
*Assistant Examiner* — Melissa S Mercier
(74) *Attorney, Agent, or Firm* — Ping Wang; Morris, Manning & Martin, LLP

(57) ABSTRACT

An object of the present invention is to provide an orally disintegrating tablet (ultrafast-disintegrating tablet) having an extremely high disintegrability (short disintegration time), and a high tablet hardness, and to provide a simple method for the production of said ultrafast-disintegrating tablet without such a complicated process as freeze-drying. This invention relates to an orally disintegrating tablet having a specific surface area of from 1.50 to 2.50 mm$^2$/mg and a weight of from 10 to 50 mg, particularly having a disintegration time in water of 7 seconds or less and an oral disintegration time of 5 seconds or less, a method for the (Continued)

(A method for the calculation of the surface area of a tablet having the radius of curvature : r)

Surface area of the spherical crown part = $2\pi rh$
Thickness (h) of the spherical crown part = $r - \sqrt{r^2 - (D/2)^2}$
Total surface area of the tablet = $4\pi rh + (L - 2h)\pi D$ production of said orally disintegrating tablet, and to a disintegrative particulate composition for use in said method.

8 Claims, 1 Drawing Sheet

(56) References Cited

FOREIGN PATENT DOCUMENTS

| WO | 2007018192 | 2/2007 |
| WO | 2013146917 | 10/2013 |
| WO | 2014046035 | 3/2014 |
| WO | 2015005241 | 3/2017 |

OTHER PUBLICATIONS

Extended European Search Report of International Application No. 15872473.2 dated Aug. 3, 2018.

* cited by examiner

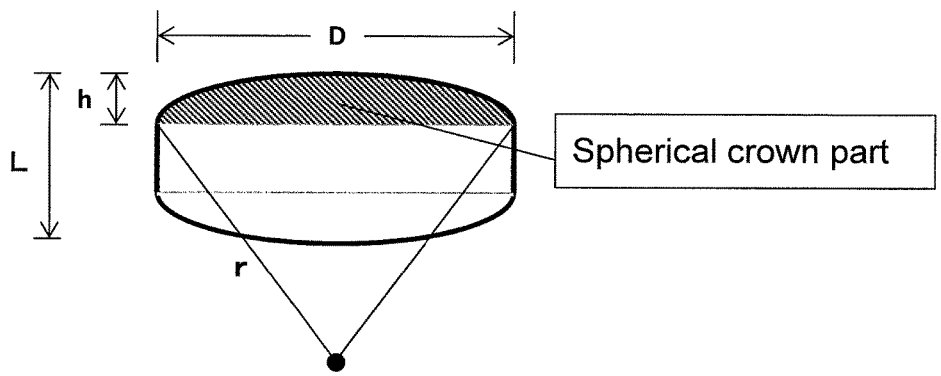
(A method for the calculation of the surface area of a tablet having the radius of curvature : r)
Surface area of the spherical crown part = $2\pi rh$
Thickness (h) of the spherical crown part = $r - \sqrt{r^2 - (D/2)^2}$
Total surface area of the tablet = $4\pi rh + (L - 2h)\pi D$

RAPIDLY DISINTEGRATING TABLET, AND METHOD FOR PRODUCING SAME

TECHNICAL FIELD

The present invention relates to an orally disintegrating tablet having an extremely short disintegration time in an oral cavity and/or in water, and an extremely high tablet hardness, and to a method for producing thereof.

BACKGROUND ART

In the past, orally disintegrating tablets have been developed as highly convenient forms which can safely be taken by patients who have difficulty in swallowing drugs, elderly people, children, etc., and which can easily be taken without water. It is important that the orally disintegrating tablets have sufficient breaking strength (tablet hardness) such that any cracks, powdering, etc. are not caused in the tablets during production or transportation of the tablets or during breaking their seals in the same manner as general tablets, and also, it is important that the orally disintegrating tablets have excellent disintegrability (disintegration time) such that the tablets immediately disintegrate in the oral cavity.

The tablet hardness and disintegrability are mutually opposing properties. In general, when a molding pressure is increased to increase the hardness, the disintegration time will tend to be prolonged, and, when the molding pressure is reduced to shorten the disintegration time, the hardness will tend to be smaller. Therefore, various technologies have been developed in order to cope with both the two properties or to achieve an optimal balance between the two properties.

Furthermore, the components of particles, granulation methods, etc. have been studied in order to impart superior moldability to the particles or particulate compositions constituting tablets.

It is well known that although the orally disintegrating tablets have improved medicine-taking compliance by patients, some patients having tendency to strongly reject the taking of medicine would vomit the tablets having the oral disintegration time in a range of bout 20-30 seconds. Accordingly, if a tablet has an extremely high disintegrability with the disintegration time of a few seconds, it can be easily administered to said patients since it will be disintegrated before they may feel uncomfortable when they take it.

Zydis (Registered Trademark) is known as a technique for the production of such tablet having an extremely high oral disintegrability, that is, an "ultrafast-disintegrating tablet." This technique has been developed by Cardinal Health Co. (Catalent Pharma Solutions, LLC) for the production of an oral solid formulation. As shown in PTL 1, it comprises preparing suspension of bulk (medicinal ingredient) and mannitol using gelatin as a supporting material and filling the suspension into a blister, followed by freeze-drying to give a rapidly dispersing solid formulation for an oral administration.

Furthermore, PTL 2 discloses an invention relating to a method for the production of a multi-phasic, lyophilized, fast-dissolving dosage form. It is prepared by sequential dosing of a formulation containing a forming agent of non-gelling matrix and a formulation containing a forming agent of gelling gelatin, followed by freeze-drying to give a multi-phasic, lyophilized, fast-dissolving dosage form (FDDF) for the delivery of a pharmaceutically active ingredient. For example, non-gelling gelatin and gelling gelatin are used for the forming agents of non-gelling matrix and gelling matrix, respectively.

RELATED ARTS

Patent Literature

PTL 1: Specification of Japanese Patent No. 4943581
PTL 2: JP-A-2013-522308

SUMMARY OF INVENTION

Problems to be solved by the Invention

However, the above-mentioned conventional techniques would require a specialized device for freeze-drying, and could not use a tablet machine for the production of an usual tablet with a high production efficiency. And, the above ultrafast-disintegrating tablet produced by the conventional techniques has an extremely low tablet hardness. It has been therefore desired an ultra- fast disintegrating tablet showing such a level of tablet hardness as allowing for a usual PTP package.

Accordingly, an object of the present invention is to solve such technical problems as found in the conventional ultrafast-disintegrating tablet, and thus, is to provide an orally disintegrating tablet (ultrafast (very rapidly)-disintegrating tablet) having such an extremely high disintegrability (short disintegration time) that a patient's taking of medicine can be certainly confirmed, and such a high tablet hardness that cracking and lacking of the tablet is expected to be reduced to a practical level. A further object of the present invention is to provide a simple method for the production of said ultrafast-disintegrating tablet without a complicated process such as freeze-drying.

Means to Solve the Problem

The present inventors found that an ultrafast-disintegrating tablet having an extremely high disintegrability can be obtained in the conventional granulation step, by using defining a particular range of properties such as weight and specific surface area of the ultrafast-disintegrating tablet, leading to completion of this invention.

More specifically, the present invention is to provide the following aspects.

[Aspect 1]
An orally disintegrating tablet having a specific surface area of from 1.50 to 2.50 $mm^2/mg$ and a weight of from 10 to 50 mg.
[Aspect 2]
The orally disintegrating tablet according to Aspect 1, which is a round-corner flat tablet with a diameter of 4 mm or less.
[Aspect 3]
The orally disintegrating tablet according to Aspect 1 or 2, having a tablet hardness of from 10 N to 21 N.
[Aspect 4]
The orally disintegrating tablet according to any one of Aspects 1 to 3, having a disintegration time in water of 7 seconds or less and an oral disintegration time of 5 seconds or less.
[Aspect 5]
The orally disintegrating tablet according to any one of Aspects 1 to 4, which comprises a first disintegrator component of an acid-type carboxymethylcellulose, and crystalline cellulose, but not bicarbonate.

[Aspect 6]

A method for the production of the orally disintegrating tablet according to any one of Aspects 1 to 5, comprising mixing a disintegrative particulate composition with a medicinal ingredient, and subjecting the resulting mixture to tableting.

[Aspect 7]

A method for the production of the orally disintegrating tablet according to Aspect 6, comprising a wet granulation step in the production of the disintegrative particulate composition.

[Aspect 8]

A method for the production of the orally disintegrating tablet according to Aspect 6 or 7, comprising a two-stage granulation step in the production of the disintegrative particulate composition.

[Aspect 9]

A method for the production of the orally disintegrating tablet according to any one of Aspects 6 to 8, wherein the tableting is carried out at a tablet compression force of from 2 to 3 kN.

[Aspect 10]

A disintegrative particulate composition comprising a first disintegrator component of an acid-type carboxymethylcellulose, for use in the method for the production of the orally disintegrating tablet according to any one of Aspects 6 to 9.

Advantageous Effects of Invention

According to the present invention, the ultrafast-disintegrating tablet having the extremely short disintegration time in the oral cavity and/or in water can be easily produced by means of such a device as used for the conventional tablets.

CONCISE EXPLANATION OF DRAWINGS

FIG. 1 shows a method for the calculation of the surface area of the orally disintegrating tablet (a tablet having R surface) according to the present invention.

DESCRIPTION OF EMBODIMENTS

The orally disintegrating tablet according to the present invention is characterized by having the specific surface area of from about 1.50 to 2.50 mm$^2$/mg, preferably of from about 1.60 to 2.30 mm$^2$/mg, and the weight of from about 10 to 50 mg, preferably of from about 15 to 30 mg.

The specific surface area means "surface area/the weight of a tablet." The surface area can be obtained by a conventional method usually done. In the case of a flat tablet, for example, it is obtained by calculating a sum of surface areas of the upper and lower circle parts and side surface (as a surface area of a round column). The specific surface area of the tablet having R surface can be obtained by the calculation shown in FIG. 1.

There is no limitation in a tablet shape in the present invention, and any shape known in the art may be adopted, such as standard R surface, sugar-coating R surface, round-corner (edge) flat tablet, angled-corner flat tablet (flat with bevel edge) and two-stage R surface. The diameter of the tablet may be optionally determined, usually being 7 mm or less, for example, about 4 mm.

From a view point of a production and use of the tablet, it is necessary for the tablet to have a relatively high hardness, being usually 10 N or more, preferably of from about 10 N to 30 N, more preferably of from about 10 N to 21 N.

It is desired to make the time for the progress of disintegration to such an extent that patients could not vomit the tablet administered any more, so that the patients won't feel uncomfortable and their vomit of the tablet will be inhibited. It is also desired to complete the disintegration and administration of the tablet as soon as possible so that the following administrations won't be rejected by the patient. Due to the above features, the tablet according to the present invention shows an extremely high disintegrability, such as the disintegration time in water of about 7 seconds or less, preferably 5 seconds or less, and the oral disintegration time (the disintegration time in an oral cavity) of 5 seconds or less, preferably 3 seconds or less, and will meet the above requirements.

Values of these physical properties were measured based on the following conditions/methods.

Hardness: a hardness (N) was measured with a Kiya hardness tester (KHT-40N, Fujiwara Scientific Company Co., Ltd.).

Disintegration time in water: a disintegration time in water was measured with a disintegration tester (NT-400, TOYAMA SANGYO CO., LTD.) in accordance with the method described in the Japanese Pharmacopoeia provided that an auxiliary disk was not used. However, the auxiliary disk was used for the tablets comprising bicarbonates.

The measurements for the hardness and disintegration time were each repeated six to ten times, and average values thereof were regarded as measurement results.

The disintegration time in water measured above is in correlation with the time for the progress of disintegration to such an extent that the patients could not vomit the tablet administered any more, and with the oral disintegration time (time for completion of the disintegration). The oral disintegration time (disintegration time in an oral cavity) was measured in Examples as follows: one tablet was taken in the oral cavity, and, while keeping a state in which the tablet was placed between the tongue and the upper jaw without applying any pressure thereto, the time required for the tablet to be completely disintegrated was measured. The measurements were each repeated three times by a few adults of both sexes, and average values thereof were regarded as measurement results.

The medicinal ingredient comprised in the orally disintegrating tablet according to the present invention includes a pharmaceutical ingredient, and nutrient ingredient comprised in foods and health food products. The medicinal ingredient may be added as such or in a coated or granulated form for the purpose of sustained release or masking of bitterness of the medicinal ingredient.

There is no limitation on the application or kind of the medicinal ingredients comprised in the orally disintegrating tablet according to the present invention, which may include, for example, agents affecting each organ such as the central nervous system, peripheral nervous system, a sensory organ, a circulatory organ, a respiratory organ and a digestive organ and an urogenital organ; hormone drug; agents affecting metabolism such as a vitamin drug, an analeptic, an agent affecting blood and body fluid; agents affecting the function of tissue and cell such as an agent activating cellular function, an agent affecting tumors, an radioactive medicine, an anti-allergic agent; medicines based on a medical prescription relating to herbal medicines and Chinese medicines; antibiotics; agents for chemotherapy, biological drug; agents for pathogenic organisms such as parasites; agents for dispersing use, diagnosis, public health and external diagnosis.

In addition to the above medicinal ingredients, the orally disintegrating tablet according to the present invention may optionally include other pharmaceutically-acceptable components such as excipients, surfactants, lubricants, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia can be used. Also, the blending ratios of each ingredient (component) are not particularly limited as long as the expected effects of the present invention are brought about, and the blending ratios can properly be determined by those skilled in the art. Furthermore, the tablet can comprise various disintegrators comprised in the following disintegrative particulate composition. The orally disintegrating tablet can be formulated by any methods known to those skilled in the art, for example, by tableting.

One of the preferable methods for the production of the orally disintegrating tablet comprises mixing the disintegrative particulate composition with the medicinal ingredient (or a pharmaceutical composition containing the medicinal ingredient) and other optional components, and subjecting the resulting mixture to tableting by means of any suitable tableting machine known in the art at a tablet compression force of from about 1 to 5 kN, preferably of from about 2 to 3 kN. Alternatively, an "externally lubricating tableting method" may be adopted, wherein a lubricant such as magnesium stearate is sprayed or applied in advance on a mortar and pestle of the tableting machine. The present invention therefore concerns the disintegrative particulate composition for use in the above method as well.

There is no limitation on the conditions (states) of the medicinal ingredients and the like, being, for example, a powdered form. Mixing (solid trituration) of the disintegrative particulate composition with the medicinal ingredient and tableting may be carried out by any method or means known to those skilled in the art. An amount of the active ingredients in the orally disintegrating tablet may be controlled to a suitable administration dose during the above steps depending on a subject, purpose and the like for the administration.

Four mechanisms of "wicking", "swelling", "deformation" and "repulsion" have been proposed as mechanisms of disintegration of tablets or the like. Among them, "wicking" is a disintegration mechanism which proceeds upon weakened binding force between particles included in the tablet as a result of water permeation through components such as disintegrators included in the tablet. As a typical example of a disintegrator having a higher effect to promote such "wicking", an acid-type carboxymethylcellulose has been known. Also, "swelling" is a disintegration mechanism which proceeds upon swelling of disintegrators themselves as a result of water permeation through the disintegrators.

The acid-type carboxymethylcellulose, which is the first disintegrator component included in the disintegrative particulate composition of the present invention, is a substance called carmellose, and has been used as a pharmaceutical additive. In the same manner as the acid-type carboxymethylcellulose, for example, both a calcium salt of carboxymethylcellulose and a cross-linked product of carboxymethylcellulose sodium are water-insoluble, and have been used as disintegrator for tablets, etc. On the other hand, a sodium salt of carboxymethylcellulose is water-soluble, and has been used for purposes of a binder, etc. In addition, in some cases, a salt of carboxymethylcellulose may be referred to as carmellose.

For the second disintegrator component of the disintegrative particulate composition of the present invention, any disintegrators other than the acid-type carboxymethylcellulose which have been known to those skilled in the art can be used. However, in order to obtain combined effects of the different disintegration mechanisms as shown above, it is preferable that a disintegrator having a superior effect to promote a mechanism other than "wicking" (e.g. "swelling") be used as the second disintegrator component. Suitable examples of such a disintegrator include crospovidone, sodium croscarmellose, sodium carboxymethyl starch, low substituted hydroxypropylcellulose, calcium carboxymethylcellulose, hydroxypropyl starch, and starch. Additionally, "crospovidone" is a common name for a cross-linked polymer of 1-vinyl-2-pyrrolidone, and "sodium croscarmellose" is a common name for a cross-linked product of sodium carboxymethylcellulose.

Among them, one, or any combination of two or more components selected from crospovidone, sodium croscarmellose, sodium carboxymethyl starch, low substituted hydroxypropylcellulose and calcium carboxymethylcellulose is preferable.

The disintegrative particulate composition further comprises an excipient. Typical examples of the excipient are sugars or sugar alcohols such as mannitol, erythritol, sorbitol, D-glucitol (maltitol), xylitol, trehalose, lactose, maltose, and. Moreover, as preferable examples thereof, mannitol erythritol, trehalose, sorbitol and D-glucitol (maltitol) can be mentioned. As the excipient, two or more types of compounds properly selected from these compounds may also be used.

The disintegrative particulate composition further comprises crystalline cellulose known to those skilled in the art in order to further improve the properties of the present disintegrating tablet. As typical examples of such crystalline cellulose, commercially-available products such as "Avicel" (FMC Corporation), "CEOLUS" (Asahi Kasei Chemicals Corp.), and "VIVAPUR" (RETTENMAIER) can be mentioned.

Furthermore, various types of optional components known to those skilled in the art may properly be added and mixed into the disintegrative particulate composition of the present invention, for the purpose of adjusting various characteristics such as the disintegrating force, binding force and ease in taking the tablet. As examples of such components, fluidizing agents, sweetening agents, flavoring agents and coloring agents can be mentioned.

It is not necessary to include gelatin or bicarbonate in the disintegrative particulate composition (or, the orally disintegrating tablet) according to the present invention, which is substantially essential as a supporting material in the prior ultrafast-disintegrating tablet for showing the desired high disintegrability.

The amount of each component blended in the disintegrative particulate composition of the present invention can properly be determined by those skilled in the art, depending on, for example, a type of the component, a type and purpose of the medicinal ingredient for which the disintegrative particulate composition is to be used, or a purpose of the final product, i.e. the orally disintegrating tablet. In general, relative to a total weight of the disintegrative particulate composition, the amount of the first disintegrator component is within a range of 10% to 50% by weight, the amount of the second disintegrator component is within a range of 1% to 20% by weight, the amount of the excipient is within a range of 30 to 88% by weight, and the amount of the crystalline cellulose is within a range of 1% to 40% by weight.

The disintegrative particulate composition according to the present invention may be produced by any method known to those skilled in the art. For example, it may be produced by a two-stage granulation step comprising a first wet granulation step using any one or two of the three components and a second wet granulation step using at least the granules obtained in the first wet granulation step and the remaining component(s) not used in the first wet granulation step, or a three-stage granulation step further comprising a third step of mixing other components with the granules obtained in the second wet granulation step.

Furthermore, the disintegrative particulate composition according to the present invention may be produced by one wet granulation step using all of the components together.

In each method of the above production method, each granulation step is carried out by a method in which each component is dispersed in the presence of water, and the dispersion is dried to form complexes, i.e. by a wet granulation process. As specific examples of a wet granulation process, spray methods such as spray drying, tumbling granulation, agitation granulation and fluidized-bed granulation; the freeze-drying method; kneading granulation, and the like can be mentioned. The composition can be produced by any of these methods known to those skilled in the art.

Since disintegrators such as an acid-type carboxymethylcellulose are hydrophilic, by carrying out a manipulation of applying a physical force such as by agitation or the like in the presence of water according to the wet granulation, the aggregated state in the dry powder will convert into a state in which particles are more dispersed. Dispersion can most easily be carried out by the fluidized-bed granulation process in which dispersion by water spraying and drying are carried out, spray drying, tumbling granulation, agitation granulation, etc., and also, drying speeds in these methods are high. Therefore, these methods are preferable.

Among them, the fluidized-bed granulation process is a granulation method in which water, an aqueous solution including a binder, or the like is sprayed onto powder, while blowing the powder up by hot air, and adjustment of spraying conditions, etc. is easy in this method. Therefore, the fluidized-bed granulation process is the most preferable method.

Furthermore, those skilled in the art can properly determine various conditions in each granulation step, such as the spraying speed, the supply air temperature, the exhaust temperature, and the air supply rate, depending on types or amounts of the components, etc.

In each granulation step, as a medium for the spray liquid, a solvent acceptable in pharmaceuticals or foods, such as water, ethanol, methanol or acetone, can be mentioned. Alternatively, as the spray liquid, for example, an aqueous solution in which less than 10% of the component(s) for the disintegrative particulate composition is dissolved can be mentioned, and, in particular, water or such an aqueous solution is preferable.

It is preferable that the disintegrative particulate composition of the present invention have the following physical properties:
(1) an average particle size of 50 to 200 microns; and
(2) a water content of 0.5% to 6% by weight.

In addition, these physical properties are measured by using the following methods and conditions.

The average particle size: 2 g of the disintegrative particulate composition is subjected to a measurement with a φ75 mm automatic shaking sieve device (Type "M-2", Tsutsui Scientific Instruments Co., Ltd.).

The water content: 5 g of the disintegrative particulate composition is subjected to a measurement using a halogen water content measuring device (Type "HB43", METTLER TOLEDO K.K.).

In addition, contents of all related art documents cited in the present specification are incorporated herein by reference.

Hereinafter, the present invention will more specifically be described with reference to Examples. However, the present invention is not considered to be limited to the Examples.

EXAMPLES (Production of the Disintegrative Particulate Composition)

In the first wet granulation step, 280 g of mannitol (D-mannitol, Merck Ltd.), 75 g of carmellose (NS-300, GOTOKU CHEMICAL CO., LTD.) and 100 g of a crystalline cellulose (CEOLUS PH-101, Asahi Kasei Chemicals Corp.) were charged to a fluidized-bed granulator (LAB-1, Powrex Corporation), and 240 g of purified water was sprayed onto the resulting mixture at a rate of 24 g/minute to thereby obtain granules. In the second wet granulation step, 40 g of crospovidone (Polyplasdone INF-10, ISP Japan) was added to the granules and 300 g of purified water was sprayed onto the resulting mixture at a rate of 10 g/minute to thereby obtain granules (a disintegrative particulate composition of the present invention). The resulting granules had the following values for physical properties: (1) an average particle size of 93 microns and (2) a water content of 2.3% by weight.

(Production of the Orally Disintegrating Tablet)

0.4 parts by weight of magnesium stearate (Taihei Chemical Industrial Co. Ltd.) as a lubricant and 0.3 parts by weight of sucralose (San-Ei Gen F.F.I., Inc.) were added to 99.3 parts by weight of the resulting granules, and these were mixed. The mixture was then subjected to tableting at tablet compression force of 2kN or 3KN with a rotating tableting machine (HT-EX12SS-U, HATA TEKKOSHO CO., LTD.) to thereby obtain a round-corner flat tablet with an diameter of 4.0 mm and a weight of from 17 to 30 mg (Examples 1-5). The physical properties of the resulting tablets are shown in Table 1 below.

TABLE 1

|  | Example 1 | Example 2 | Example 3 | Example 4 | Example 5 |
| --- | --- | --- | --- | --- | --- |
| Tablet Weight (mg) | 17 | 17 | 21 | 21 | 30 |
| Tablet Thickness (mm) | 1.06 | 1.05 | 1.31 | 1.26 | 1.86 |
| Surface Area (mm$^2$) | 38.4 | 38.3 | 41.6 | 41.0 | 48.5 |
| Specific Surface Area (mm$^2$/mg) | 2.26 | 2.25 | 1.98 | 1.95 | 1.62 |
| Tablet compression Force (kN) | 2 | 3 | 2 | 3 | 2 |
| Tablet Hardness (N) | 11.8 | 16.6 | 13.9 | 20.4 | 20.9 |

TABLE 1-continued

| | Example 1 | Example 2 | Example 3 | Example 4 | Example 5 |
|---|---|---|---|---|---|
| Disintegration time in water (seconds) | 4 | 5 | 4 | 7 | 7 |
| Oral Disintegration time (seconds) | 3 | 4 | 3 | 5 | 4 |

The data in Table 1 show that the orally disintegrating tablet according to the present invention has such an excellent disintegrability such as the extremely short disintegration time in water and in the oral cavity.

INDUSTRIAL APPLICABILITY

The present invention has enabled to provide an orally disintegrating tablet (ultrafast-disintegrating tablet) having not only advantages that it can safely be taken by patients who have difficulty in swallowing drugs, elderly people, children, etc. and can easily be taken without water, but also further advantages that it has such an extremely high disintegrability (short disintegration time) that the taking of medicine by patients having tendency to strongly reject it can be certainly confirmed, and such a high tablet hardness that cracking and lacking of the tablet is expected to be reduced to a practical level.

The invention claimed is:

1. An orally disintegrating tablet having a specific surface area of from 1.60 to 2.50 $mm^2$/mg, a weight of from 10 to 30 mg, and a diameter of 4 mm or less, which comprises a disintegrative particulate composition containing crystalline cellulose in an amount of 1% to 40% by weight of a total weight of the composition, and has a disintegration time in water of 7 seconds or less and an oral disintegration time of 5 seconds or less.

2. The orally disintegrating tablet according to claim 1, having a tablet hardness of from 10 N to 21 N.

3. The orally disintegrating tablet according to claim 1, which comprises carmellose and crystalline cellulose, wherein the composition does not contain a bicarbonate.

4. A method for the production of the orally disintegrating tablet according to claim 1, comprising mixing a disintegrative particulate composition with a medicinal ingredient, and subjecting the resulting mixture to tableting.

5. The method for the production of the orally disintegrating tablet according to claim 4, further comprising a wet granulation step in the production of the disintegrative particulate composition.

6. The method for the production of the orally disintegrating tablet according to claim 4, further comprising a two-stage granulation step in the production of the disintegrative particulate composition.

7. The method for the production of the orally disintegrating tablet according to claim 4, wherein the tableting is carried out at a tablet compression force of from 2 to 3 kN.

8. The orally disintegrating tablet according to claim 2, which comprises carmellose and crystalline cellulose, wherein the composition does not contain a bicarbonate.

* * * * *